US00PP35427P2

(12) United States Plant Patent
Avent

(10) Patent No.: US PP35,427 P2
(45) Date of Patent: Oct. 17, 2023

(54) ***ALSTROEMERIA* PLANT NAMED 'GOLDEN TIARA'**

(50) Latin Name: ***Alstroemeria* hybrid**
Varietal Denomination: Golden Tiara

(71) Applicant: Tony Avent, Raleigh, NC (US)

(72) Inventor: Tony Avent, Raleigh, NC (US)

( * ) Notice: Subject to any disclaimer, the term of this patent is extended or adjusted under 35 U.S.C. 154(b) by 5 days.

(21) Appl. No.: 17/803,748

(22) Filed: Nov. 8, 2022

(51) Int. Cl.
*A01H 5/02* (2018.01)
*A01H 6/00* (2018.01)

(52) U.S. Cl.
USPC ..... Plt./309

(58) Field of Classification Search
USPC ..... Plt./263.1, 309
See application file for complete search history.

(56) References Cited

U.S. PATENT DOCUMENTS

PP24,128 P2 * 12/2013 Tas ..... A01H 5/02
Plt./309

* cited by examiner

*Primary Examiner* — Karen M Redden

(57) ABSTRACT

A new and unique cultivar of *Alstroemeria* plant named 'Golden Tiara', characterized by its large, upwardly to outwardly spreading and mounded plant habit, moderately to rapid growth rate, producing numerous gold-colored flowers with complementing coral-orange throat, suitable for container and garden landscape performance in areas winter hardy to USDA zone 6.

2 Drawing Sheets

Botanical denomination: *Alstroemeria* hybrid.
Cultivar designation: 'Golden Tiara'.

STATEMENT REGARDING PRIOR DISCLOSURES UNDER 37 CFR 1.77(b)(6)

The first sale of the claimed plant was made on Nov. 15, 2021, by Walters Gardens, Inc. to Plant Delights Nursery, Inc. Subsequently, the plant appeared on Jan. 1, 2022, on the Plant Delights Nursery, Inc. website, and on Feb. 1, 2022, as a photograph and brief description in the Walters Gardens, Inc. website followed by the "Walters Gardens 2022-2023 Catalog" first distributed to customers on Jun. 8, 2022. Walters Gardens, Inc. and Plant Delights Nursery, Inc. both obtained the plant and all information relating thereto, from the inventor. No plants of *Alstroemeria* 'Golden Tiara' have been sold, in this country or anywhere in the world, nor has any disclosure of the new plant been made more than one year prior to the filing date of this application, and such sale or disclosure within one year was either derived directly or indirectly from the inventor and would therefore be a 35 U.S.C. § 102b exception.

BACKGROUND OF THE INVENTION

The present invention relates to a new and distinct cultivar of *Alstroemeria* plant, botanically known as *Alstroemeria* hybrid, commercially used as a potted and garden-type *Alstroemeria*, and hereinafter referred to by the name 'Golden Tiara'.

The new *Alstroemeria* plant was discovered in March of 2018, as a whole plant mutation in a batch of 'Koice' (not patented) at a nursery in Raleigh, N.C. 'Golden Tiara' was then propagated by rhizome shoot tip tissue culture in the fall of 2019 and later propagated by division at the same nursery. The new plant passed final evaluation at a whole perennial nursery in Zeeland, Mich. The new plant has also been propagated by tissue culture rhizogenesis with both division and tissue culture asexual propagation methods proving the unique features of this new *Alstroemeria* plant are stable and reproduced true to type in successive generations.

SUMMARY OF THE INVENTION

Plants of 'Golden Tiara' have not been observed under all possible combinations of environmental conditions and cultural practices. The phenotype may vary somewhat with variations in environmental conditions such as temperature and light intensity without, however, any variance in genotype.

*Alstroemeria* 'Golden Tiara' is distinct from its parent and all other *Alstroemeria* known to the applicant in the following combined traits:

1. Large, upwardly to outwardly spreading and mounded plant habit;
2. Moderately vigorous to vigorous growth habit and moderate to rapid growth rate;
3. Numerous gold-colored flowers with complementing coral-orange throat;
4. Excellent container and garden performance;
5. Winter hardy to at least USDA zone 6.

Plants of the new *Alstroemeria* can be compared to plants of the mutation parent, 'Koice'. Plants of 'Koice' have blushing coral-pink and white flowers with darker bar markings. Plants of the new *Alstroemeria* can be compared to: 'Zapriyen' U.S. Plant Pat. No. 34,018 has white flowers with yellow centers and the size is much smaller in habit. 'Zoe' U.S. Plant Pat. No. 30,680 has light red-colored flowers with yellow centers, fewer flowers per inflorescence, and the inflorescences are much shorter.

BRIEF DESCRIPTION OF THE DRAWINGS

The accompanying color photographs of the new invention are of a two-year-old plant grown in full-sun trial garden and illustrate the overall appearance of the plant including the unique traits. The colors are as accurate as reasonably possible with color reproductions. Some slight variations of color may occur as a result of lighting quality, intensity, wavelength, direction, or reflection.

DETAILED DESCRIPTION OF THE PLANT

Figure 1:
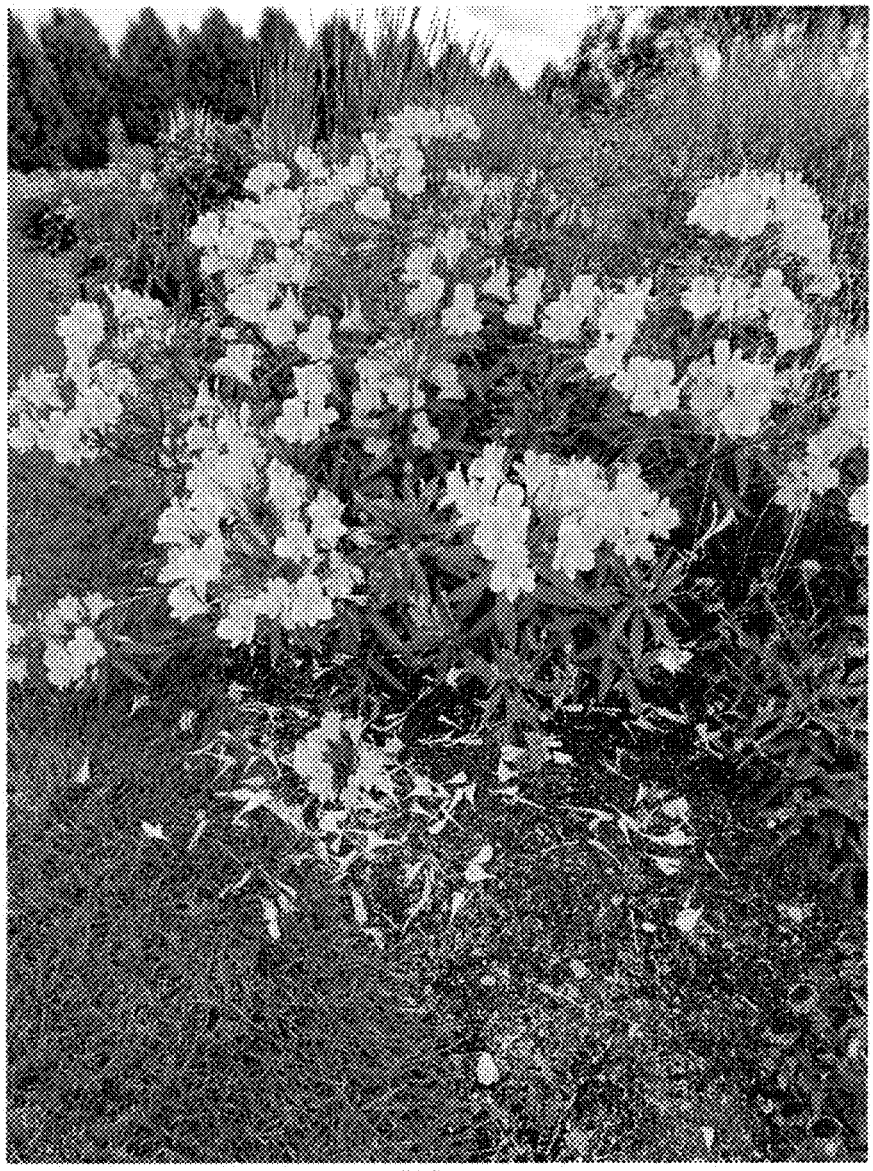
FIG. 1 shows the habit of the plant in mid-season flowering.
Figure 2:
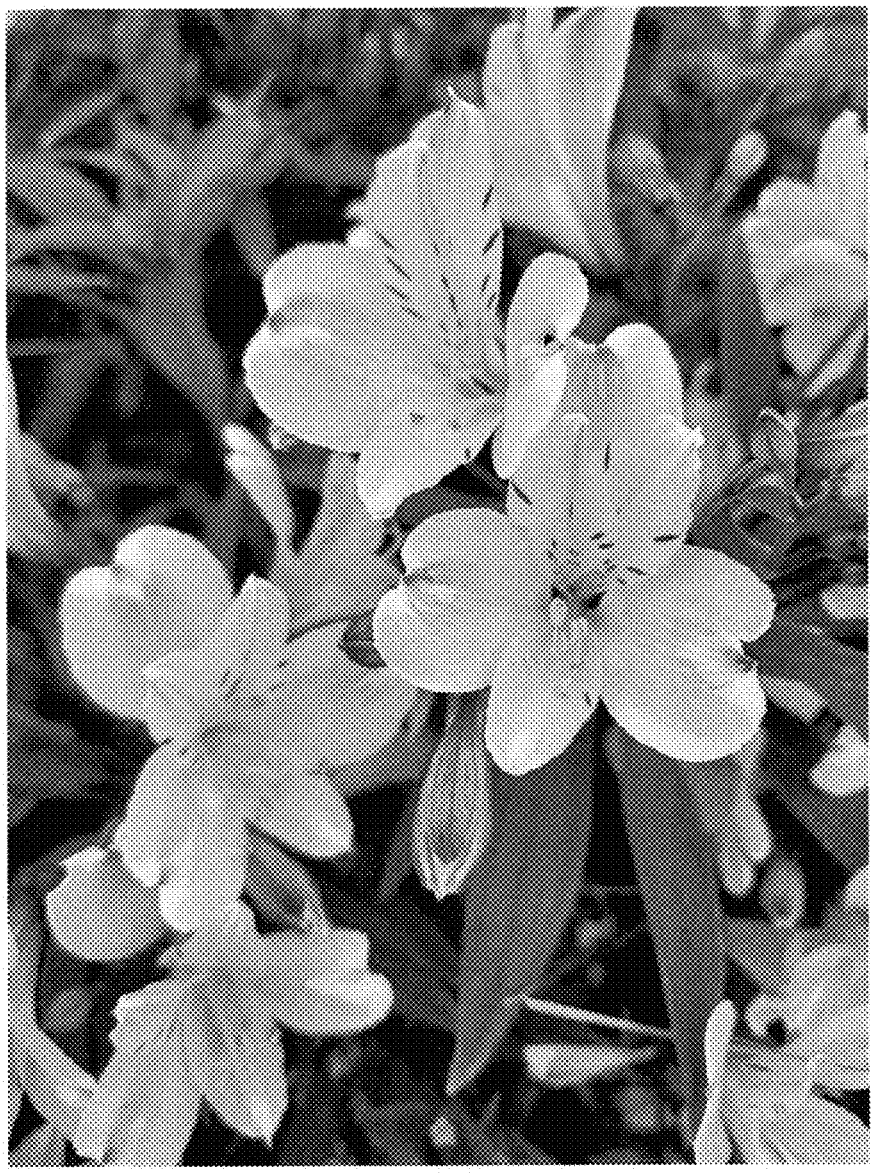
FIG. 2 shows a close-up of the flowers and buds.

The aforementioned photographs and following observations and measurements describe plants of the new *Alstroemeria* grown in a full-sun display garden in Zeeland, Mich. The plants were two years old when the photographs and descriptions were taken. In the following description, color references are made to The Royal Horticultural Society Colour Chart, 2015 Edition, except where general terms of ordinary dictionary significance are used.

Botanical classification: *Alstroemeria* hybrid 'Golden Tiara'.

Parentage: Mutation parent was 'Koice'.

Propagation: Tissue culture rhizogenesis.

Time to produce a rooted young plant: About four weeks at temperatures of 16° C. to 25° C.

Root description: Fibrous, fleshy, thick, freely-branching; medium density; color nearest RHS 155D.

Rhizomes: Elongate; cylindrical; glabrous; matte; to about 15 cm long and about 6 mm diameter at base.

Rhizome color: Nearest RHS 155D.

Plant habit: Dense upright to outwardly spreading stems forming tall rounded mound; typically unbranched; vigorous rapid growth; to about 100 cm tall and 140 cm wide about 30 cm above soil.

Stem: To about 80 stems per plant; cylindrical; glabrous; slightly glaucous; lustrous once bloom is worn away; aspect vertical to about 45° outwardly; to about 95 cm long and 9 mm diameter at base.

Stem color: Proximally nearest RHS 146D variably speculate to nearly solid patches of nearest RHS N186C distally nearest RHS 146B variably speculate to nearly solid patches of nearest RHS N186C.

Nodes: About 31 per stem above soil line; average internode length about 2.6 cm.

Node color: Nearest RHS 146B.

Leaf description: Alternate; simple; lanceolate-linear; acute apex; cuneate truncate base; entire margin; glabrous adaxial and abaxial; adaxial slightly lustrous; abaxial slightly glaucous; to about 106 mm long and 22 mm wide; aspect upright to horizontal; twisting near base, resupinate.

Leaf color: Young developing adaxial and abaxial nearest RHS 146B; mature adaxial nearest RHS 137A and abaxial nearest RHS 137B.

Venation: Parallel; glabrous adaxial and abaxial; slightly lustrous and indented adaxial and abaxial slightly glaucous and costate.

Vein color: Developing leaves adaxial nearest 137B, abaxial nearest RHS 146B; mature adaxial nearest RHS 137A, abaxial nearest RHS 144A.

Petioles: Flattened; twisted; slightly lustrous adaxial and slightly glaucous abaxial; to about 2.5 cm long and 6.5 mm wide at base.

Petiole color: Adaxial nearest RHS 137A and abaxial nearest RHS 137B.

Inflorescence: Compound umbel with eight primary stems having about four flowers each; flowering in the distal 12 cm to about 17 cm wide; primary stems joined at base and each stem and branch subtended by a single leaf to about 10 cm long and 2 cm wide; with about 6 to 27 flowers per inflorescence.

Primary umbel stems: Slightly flattened to about 6 cm long to first branch and 3 mm wide and 2 mm thick; color nearest RHS 146C variably speculate to nearly half nearest RHS N186C.

Flower: Single; campanulate; incomplete; perfect; flowers face upright to outwardly; perianth segments separate; freely flowering habit with about 15 flowers average per inflorescence and about 200 flower buds and flowers developing per plant at one time.

Flowering season: Flowering continuously with new stems from the spring until the autumn.

Fragrance: None detected.

Flower longevity: On the plant or as a cut flower for about 1.5 weeks; flowers not persistent.

Flower buds: Obovoid with long narrow base; surface glabrous and matte; to about 35 mm long, enlarged distal bulb portion to about 10 mm diameter and base tapering down to about 5 mm diameter at ovary.

Bud color: Variable depending on light exposure; dorsal portion nearest RHS 183A in basal one-half, distal one-half between RHS 147B and RHS 183B; ventral portion nearest RHS 145C in basal two-thirds transitioning to nearest RHS 138A with tinting of nearest RHS 183B in apical 5 mm.

Flower size: About 54 mm wide, about 65 mm tall, and 55 mm deep.

Perianth: Six arranged in two whorls; each whorl with two lateral and one median segments.

Inner whorl lateral segments: Oblanceolate; about 60 mm long and 19 mm wide toward apex; ribbed with two longitudinal ribs distally; basal 15 mm enrolled; apex acute and pinched; base attenuate; margin crenate distally, middle entire, and proximally ciliolate; adaxial surface texture and luster glabrous, semi-glossy; abaxial surface texture and luster glabrous and semi-glossy; color adaxial when opening and fully opened apex between RHS 13A and RHS 12A, with longitudinal bars about 0.7 mn wide of variable lengths between 1.5 mm and 5 mm long of nearest RHS N79A, about 15 to 25 mm from base nearest RHS 36A, and basal 10 mm nearest RHS 146C, abaxial distal three midribs nearest RHS 146C, distally between RHS 13A and RHS 12A with a blush of nearest RHS 146D in the distal 5 mm, with about 15 to 25 bars variably colored of nearest RHS 178B, and a blend between RHS N199A and RHS 183B, middle portion between RHS 37A and RHS 37B, and basal 10 to 15 mm nearest RHS 146D with a strong blush of nearest RHS 183A; inner center ventral perianth oblanceolate, about 49 mm long and 17 mm wide; apex acute and pinched, base attenuate, margin crenate; with pinched midrib producing a longitudinal dorsal ridge, color adaxial distal 25 mm between RHS 13A and RHS 12A with 2 to 4 bars about 2 to 3 mm long and 0.7 mm wide nearest RHS N79A, basal 5 mm nearest RHS 146D and portion between base and distal area nearest RHS NN155C; color abaxial distal 25 mm between RHS 12B and RHS 13B, with 2 to 4 bars variably colored of nearest RHS 178B, and a blend between RHS N199A and RHS 183B, basal 5 mm between RHS 146C and RHS 146D, portion between base and distal nearest RHS NN155C; outer lateral and dorsal perianth oblanceolate, to about 52 mm long and 27 mm wide, apex rounded and broadly emarginate, adaxial and abaxial glabrous, semi-lustrous, base attenuate and enrolled in proximal 10 mm, margin serrulate; adaxial color at indented apex nearest RHS 146A, distal one half nearest RHS 12A near center and lightening to nearest RHS 12C near margin, basal 5 mm nearest RHS 146D, with portion in middle nearest RHS 27C, abaxial color in distal 25 mm along the 5 mm margin between RHS 13B and RHS 13C, center nearest RHS 13B maculate with small irregular spots of 1 mm diameter nearest RHS 183B, middle portion nearest RNS N45D.

Pedicels: To about 22 mm long and 2 mm across; strong, stiff; with longitudinal ridges; aspect upright to outwardly; smooth, glabrous; semi-glossy.

Pedicel color: Nearest RHS 146A distally and nearest RHS 146C proximally with ridges moderately blushed with nearest RHS 183B.

Androecium: Typically six; maturing in sets of three.

*Filaments.*—Six; cylindrical, semi-planate proximally; glabrous, semi-lustrous; to about 44 mm long and 1.5 mm across, and 1 mm thick at base.

*Filament color.*—Between RHS 145D and RHS 146D proximally, nearest RHS 37D in the middle portion, and nearest RHS 10D distally.

*Anther.*—Basifixed; longitudinal; ellipsoidal; to about 8 mm long and 2.5 mm across.

*Anther color.*—Nearest RHS 162A.

*Pollen.*—Abundant; color Close to 14A.

Gynoecium: Single; to about 55 mm long.

*Style.*—Straight; angular, with longitudinal ridges; about 36 mm long and 2 mm across at base.

*Style color.*—Nearest RHS 145D proximally, center nearest RHS 27C, distally nearest RHS 4B.

*Stigma.*—Typically trifurcate; semi-lustrous and micropuberulent adaxial, and glabrous and semi-lustrous abaxial; about 8 mm long and about 0.5 mm diameter.

*Stigma color.*—Nearest 5C.

*Ovary.*—Inferior; about 12 mm long and 7 mm across; acute apex and rounded base; with longitudinal ridges.

*Ovary color.*—Nearest RHS 138A with ridges moderately blushed with nearest RHS 178A.

Fruit: Dehiscent capsule; six-sided ovoid; acute apex; rounded base; carinate with three main ridged and three smaller ridges between the large ridges extending from base to about 4 mm from apex; to about 21 mm long and 16 mm across near middle; color when dried nearest RHS 164C between carinae and carinae nearest RHS 165A.

Seeds: To date, seed development has not been observed on plants of the new *Alstroemeria*.

Pathogen and pest resistance: To date, plants of the new *Alstroemeria* have not been observed to be resistant to pathogens and pests common to *Alstroemeria* plants.

Garden performance: Plants of the new *Alstroemeria* have been observed to have excellent garden performance and to tolerate wind, rain, and temperatures from about −20° C. to about 38° C. and to be suitable for USDA winter hardiness to zone 6.

It is claimed:

1. A new and distinct *Alstroemeria* plant named 'Golden Tiara' essentially as herein described and illustrated. .

* * * * *